United States Patent [19]

Wu et al.

[11] 4,427,441
[45] Jan. 24, 1984

[54] PHTHALIMIDES OF PHENOXYBENZOIC ACIDS

[75] Inventors: Frank Wu, Libertyville; Leonard J. Stach, Riverside, both of Ill.

[73] Assignee: Velsicol Chemical Corporation, Chicago, Ill.

[21] Appl. No.: 410,679

[22] Filed: Aug. 23, 1982

[51] Int. Cl.³ .................. A01N 43/38; C07D 209/48
[52] U.S. Cl. .................................. 71/96; 548/479
[58] Field of Search .................... 548/479; 71/96

[56] References Cited

U.S. PATENT DOCUMENTS 3,950,307  4/1976  Richter et al. ............... 548/479
4,093,446  6/1978  Bayer et al. .................. 71/88

FOREIGN PATENT DOCUMENTS 1120034  3/1982  Canada .
1140547  2/1983  Canada .

Primary Examiner—Donald G. Daus
Assistant Examiner—M. C. Eakin
Attorney, Agent, or Firm—Robert J. Schwarz

[57] ABSTRACT

This invention discloses novel herbicidal chemical compounds of the formula

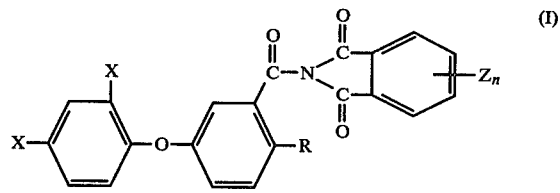

wherein X is halogen or trifluoromethyl; Y is selected from the group consisting of hydrogen, halogen, nitro and cyano; R is selected from the group consisting of nitro, alkylthio, halogen and cyano; Z is selected from the group consisting of alkyl, halogen and nitro; and n is an integer from 0 to 4.

10 Claims, No Drawings

PHTHALIMIDES OF PHENOXYBENZOIC ACIDS

This invention relates to new compositions of matter and more specifically relates to new chemical compounds of the formula:

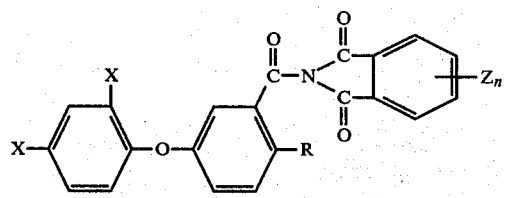

wherein X is halogen or trifluoromethyl; Y is selected from the group consisting of hydrogen, halogen, nitro and cyano; and R is selected from the group consisting of nitro, alkylthio, halogen and cyano; Z is selected from the group consisting of alkyl, halogen and nitro; and n is an integer from 0 to 4.

The compounds of the present invention are unexpectedly useful as selective herbicides.

In a preferred embodiment of the present invention X is chlorine, bromine or trifluoromethyl; Y is hydrogen, chlorine, bromine, nitro or cyano; R is nitro, methylthio, chlorine, bromine and cyano; Z is selected from the group consisting of alkyl of up to six carbon atoms, chlorine, bromine and nitro; and n is an integer from 0 to 2.

The compounds of the present invention can be prepared by reacting an acid chloride of the formula

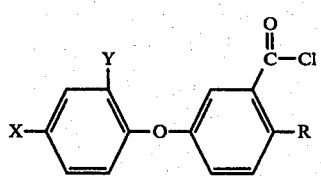

wherein X, Y and R are as heretofore described with an alkali metal salt of the formula

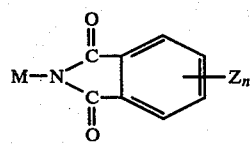

wherein M is an alkali metal such as sodium or potassium and Z and n are as heretofore described.

This reaction can be conveniently effected by combining equimolar amounts of the acid chloride and the phthalimide salt in an inert organic reaction medium such as dimethylformamide. The reaction mixture can be stirred at room temperature for a period of several hours to ensure completion of the reaction. After this time the mixture can be poured into water and extracted with an organic solvent such as toluene. The extract is then stripped of solvent to yield the desired product which can be used as such or can be further purified by conventional techniques such as recrystallization and the like.

The acid chloride of formula II useful in preparing the compounds of the present invention can be readily prepared from the corresponding acid by reaction with thionyl chloride. This reaction can be conveniently effected by combining the acid and thionyl chloride in an organic solvent such as toluene and heating the mixture at reflux temperature for a period sufficient to ensure completion of the reaction. The reaction mixture can then be stripped of solvent to yield the desired acid chloride.

Exemplary precursor acid for the acid chloride of formula II are 2-nitro-5-(2-chloro-4-trifluoromethylphenoxy)benzoic acid, 2-nitro-5-(2,4-dichlorophenoxy)benzoic acid, 2-nitro-5-(2-nitro-4-chlorophenoxy)benzoic acid, 2-nitro-5-(2-cyano-4-trifluoromethylphenoxy)benzoic acid, 2-nitro-5-(4-trifluoromethylphenoxy)benzoic acid, 2-methylthio-5-(2-chloro-4-trifluoromethylphenoxy)benzoic acid, 2-chloro-5-(2-chloro-4-trifluoromethylphenoxy)benzoic acid, 2-bromo-5-(2-chloro-4-trifluoromethylphenoxy)benzoic acid, 2-ethylthio-5-(2-chloro-4-trifluoromethylphenoxy)benzoic acid, 2-propylthio-5-(2-chloro-4-trifluoromethylphenoxy)benzoic acid, 2-cyano-5-(2-chloro-4-trifluoromethylphenoxy)benzoyl chloride and the like.

Exemplary phthalimide salts useful for preparing the compounds of the present invention are the sodium or potassium salts of phthalimide, 4-methylphthalimide, 4-chlorophthalimide, 4-methyl-5-chlorophthalimide, 4,5-dimethylphthalimide, 4-ethylphthalimide, 4-propylphthalimide, 4-hexylphthalimide, 4-bromophthalimide, 4-fluorophthalimide, 4-nitrophthalimide, 5-nitrophthalimide and the like.

The manner in which the compounds of the present invention can be prepared is more specifically illustrated in the following examples.

EXAMPLE 1

Preparation of 2-Nitro-5-(2-chloro-4-trifluoromethylphenoxy)benzoyl chloride

2-Nitro-5-(2-chloro-4-trifluoromethylphenoxy)benzoic acid (80 grams) and toluene (80 ml) were charged into a reaction vessel equipped with a mechanical stirrer, thermometer and reflux condenser. Thionyl chloride (80 ml) was slowly added at room temperature with stirring. After the addition was completed the mixture was heated at reflux with continued stirring for a period of one hour. Stirring was thereafter continued at room temperature overnight. Aftr this time the reaction mixture was stripped of toluene to yield the desired product 2-nitro-5-(2-chloro-4-trifluoromethylphenoxy)benzoyl chloride.

EXAMPLE 2

Preparation of N-[2-Nitro-5-(2-chloro-4-trifluoromethylphenoxy)benzoyl]phthalimide The N-potassium salt of phthalimide (4.63 grams; 0.025 mole) dissolved in dimethylformamide (50 ml) was charged into a glass reaction vessel equipped with a mechanical stirrer and thermometer. 2-Nitro-5-(2-chloro-4-trifluoromethylphenoxy)benzoyl chloride (9.5 grams; 0.025 mole) was added and the reaction mixture was stirred at room temperature overnight. After this time the mixture was poured into water and was thereafter extracted with toluene. The toluene extract was evaporated to dryness leaving a dark reddish solid. This solid was recrystallized from toluene to yield the desired product N-[2-nitro-5-(2-chloro-4-trifluoromethylphenoxy)benzoyl]phthalimide as a white powder melting at 160° C.

EXAMPLE 3

Preparation of N-[2-Methylthio-5-(2-chloro-4-trifluoromethylphenoxy)benzoyl]phthalimide The N-potassium salt of phthalimide (0.025 mole) dissolved in dimethylformamide (50 ml) and 2-methylthio-5-(2-chloro-4-trifluoromethylphenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-methylthio-5-(2-chloro-4-trifluoromethylphenoxy)benzoyl]phthalimide.

EXAMPLE 4

Preparation of N-[2-Chloro-5-(4-trifluoromethylphenoxy)benzoyl]phthalimide

The N-potassium salt of phthalimide (0.025 mole) dissolved in dimethylformamide (50 ml) and 2-chloro-5-(4-trichloromethylphenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-chloro-5-(4-trifluoromethylphenoxy)benzoyl]phthalimide.

EXAMPLE 5

Preparation of N-[2-Cyano-5-(2,4-dichlorophenoxy)benzoyl]phthalimide

The N-potassium salt of phthalimide (0.025 mole) dissolved in dimethylformamide (50 ml) and 2-cyano-5-(2,4-dichlorophenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-cyano-5-(2,4-dichlorophenoxy)benzoyl]phthalimide.

EXAMPLE 6

Preparation of N-[2-Nitro-5-(2-cyano-4-trifluoromethylphenoxy)benzoyl]phthalimide The N-potassium salt of phthalimide (0.025 mole) dissolved in dimethylformamide (50 ml) and 2-nitro-5-(2-cyano-4-trifluoromethylphenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-nitro-5-(2-cyano-4-trifluoromethylphenoxy)benzoyl]phthalimide.

EXAMPLE 7

Preparation of N-[2-Chloro-5-(2-chloro-4-trifluoromethylphenoxy)-benzoyl]phthalimide The N-potassium salt of phthalimide (0.025 mole) dissolved in dimethylformamide (50 ml) and 2-chloro-5-(2-chloro-4-trifluoromethylphenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-chloro-5-(2-chloro-4-trifluoromethylphenoxy)benzoyl]phthalimide.

EXAMPLE 8

Preparation of N-[2-Nitro-5-(2-Chloro-4-trifluoromethylphenoxy)benzoyl]-B 4-methylphthalimide The N-potassium salt of 4-methylphthalimide (0.025 mole) dissolved in dimethylformamide (50 ml) and 2-nitro-5-(2-chloro-4-trifluoromethylphenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-chloro-5-trifluoromethylphenoxy)benzoyl]-4-methylphthalimide.

EXAMPLE 9

Preparation of N-[2-Cyano-5-(2,4-dichlorophenoxy)benzoyl]-4-chlorophthalimide

The N-potassium salt of 4-chlorophthalimide (0.025 mole) dissolved in dimethylformamide (50 ml) and 2-cyano-5-(2,4-dichlorophenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-cyano-5-(2,4-dichlorophenoxy)benzoyl]-4-chlorophthalimide.

EXAMPLE 10

Preparation of N-[2-Nitro-5-(2-Cyano-4-trifluoromethylphenoxy)benzoyl]-4-methyl-5-chlorophthalimide The N-potassium salt of 4-chloro-5-chlorophthalimide (0.025 mole) dissolved in dimethylformamide (50 ml) and 2-nitro-5-(2-cyano-4-trifluoromethylphenoxy)-benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-nitro-5-(2-cyano-4-trifluoromethylphenoxy)benzoyl]-4-methyl-5-chlorophthalimide.

EXAMPLE 11

Preparation of N-[2-Bromo-5-(2-nitro-4-bromophenoxy)benzoyl]-4-nitrophthalimide The N-potassium salt of 4-nitrophthalimide (0.025 mole) dissolved in dimethylformamide (50 ml) and 2-bromo-5-(2-nitro-4-bromophenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-bromo-5-(2-nitro-4-bromophenoxy)benzoyl]-4-nitrophthalimide.

EXAMPLE 12

Preparation of N-[2-Nitro-5-(2,4-dibromophenoxy)benzoyl]-4-propylphthalimide The N-potassium salt of 4-propylphthalimide (0.025 mole) dissolved in dimethylformamide (50 ml) and 2-nitro-5-(2,4-dibromophenoxy)benzoyl chloride (0.025 mole) are charged into a glass reaction vessel equipped with a mechanical stirrer and thermometer. The reaction mixture is stirred at room temperature for a period of about 8 hours. After this time the mixture is poured into water (150 ml) and is extracted twice with toluene. The toluene extracts are combined and stripped of solvent leaving a solid residue. This residue is recrystallized to yield the desired product N-[2-nitro-5-(2,4-dibromophenoxy)benzoyl]-4-propylphthalimide.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wettable agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 13

Preparation of a Dust

| Product of Example 2 | 10 |
|---|---|
| Powdered Talc | 90 |

The above ingredients are mixed in a mechanical grinder blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 15% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4-(2,4-DB), 2,4-DEB, 4-DPB, 4CPP, 2,4,5-TB, 2,4,5-TES, 3,4-DA, silvex and the like; carbamate; herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isoproppyl acetamide, 2-chloro-Nisopropylacetanalide, 4-(chloroacetyl)-morpholine, 1-(chloroacetyl) piperidine, and the like; chlorinated aliphatic acid herbicides such as TCA, dalapon, 2,3-dichloropropionic acid, 2,2,3-TPA and the herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 15% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4-(2,4-DB), 2,4-DEB, 4-DPB, 4CPP, 2,4,5-TB, 2,4,5-TES, 3,4-DA, silvex and the like; carbamate; herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alphachloro-N,N-dimethylacetamide, CDEA, CDAA, alpha-chloro-N-isopropyl acetamide, 2-chloro-N-isopropylacetanalide, 4-(chloroacetyl)-morpholine, 1-(chloracetyl) piperidine, and the like; chlorinated aliphatic acid herbicides such as TCA, dalapon, 2,3-dichloropropionic acid, 2,2,3-TPA and the like; chlorinated benzoic acid and the phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, DMA, DPMF, cypromid, DBC, DCPA, dichlone, diphenatril, DMTT, DNAP, EBEP, EXD, HCA, ioxynil, IPX, isocyil, potassium cyanate, MAA, MAMA, MCPES, MCP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindone B, propanil and the like.

Such herbicides can also be used in the methods and composition of this invention in the form of their salts, esters, amides and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitroy, groundsel, hemp nettle, knowel, spurge, spurry, emex, jungle rice, pondweed, dog fennel, carpetweed, mornigglory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

Afer spraying, the soil containers were placed in the green house and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged. The effectiveness of these compounds is demonstrated by the following data set out in Table 1. Numbers with decimal places are the result of averaging two or more ratings obtained from replicate experiments.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 10 to 15 days after treatment and was rated on the scale of from 0 to 10 heretobefore described. The effectiveness of these compounds is demonstrated by the following data set forth in Table II. Values with decimal places again are the result of averaging of replicate experiments.

TABLE I

Pre-Emergence Screen
14 & 21-Day Testing

| Compound | #/Acre | WMSD 14 | 21 | BDWD 14 | 21 | PIGW 14 | 21 | JMWD 14 | 21 | VTLF 14 | 21 | MNGY 14 | 21 | YLFX 14 | 21 | BNGS 14 | 21 | JNGS 14 | 21 |
|---|---|---|---|---|---|---|---|---|---|---|---|---|---|---|---|---|---|---|---|
| Product of | 8 | 10 | 10 | — | — | 10 | 10 | 10 | 10 | 10 | 10 | 8 | 10 | — | — | 10 | 10 | 10 | 10 |
| Example 2 | 4 | NE | NE | — | — | NE | NE | NE | NE | NE | NE | 9 | 8 | 5 | 8 | 9 | 10 | 9 | 9 |
| | 2 | NE | NE | — | — | NE | NE | NE | NE | NE | NE | 4 | 4 | NE | 8 | 9 | 9 | 7 | 9 |
| | 1 | 10* | 10* | 5 | 4 | 10* | 10* | 8* | 9* | NE* | NE* | 7* | 6* | 6* | 6* | 8* | 8* | 8.5* | 10* |
| | .5 | 10 | 10 | 4 | 2 | 7 | 10 | NE | NE | 10 | 10 | 6 | 1 | 6 | 4 | 9 | 9 | 7 | 7 |
| | .25 | 10 | 10 | 0 | 0 | 7 | 10 | NE | NE | 2 | 0 | 5 | 1 | 2 | 0 | 2 | 0 | 3 | 4 |
| | .125 | 1 | 2 | 0 | 0 | 2 | 7 | 3 | 0 | 0 | 0 | 0 | 0 | 0 | 0 | 0 | 0 | 2 | 3 |

| Compound | #/Acre | QKGS 14 | 21 | WOAT 14 | 21 | CBGS 14 | 21 | SUBT 14 | 21 | YLFX 14 | 21 | CTGS 14 | 21 | YNSG 14 | 21 | SOYB 14 | 21 | COTN 14 | 21 |
|---|---|---|---|---|---|---|---|---|---|---|---|---|---|---|---|---|---|---|---|
| Product of | 8 | — | — | 10 | 10 | 10 | 10 | — | — | 6 | 8 | 10 | 10 | NE | NE | — | — | — | — |
| Example 2 | 4 | — | — | 9 | 9 | NE | NE | — | — | — | — | NE | 10 | 1 | 5 | — | — | — | — |
| | 2 | — | — | 2 | 8 | 10 | 10 | — | — | — | — | 5 | 5 | 0 | 0 | — | — | — | — |
| | 1 | NE | NE | 6* | 6* | 10* | 9.5* | 10 | 10 | — | — | 0 | 0 | 0 | 0 | 3 | 1 | 0 | 0 |
| | .5 | 3 | 3 | 1 | 3 | 10 | 10 | 10 | 10 | — | — | — | — | — | — | 0 | 0 | 0 | 0 |
| | .25 | 1 | 0 | 0 | 0 | 9 | 10 | 10 | 10 | — | — | — | — | — | — | 0 | 0 | 0 | 0 |
| | .125 | 0 | 0 | 0 | 0 | 0 | 0 | 0 | 0 | — | — | — | — | — | — | 0 | 0 | 0 | 0 |

| Compound | #/Acre | PTBN 14 | 21 | ALFA 14 | 21 | WHT 14 | 21 | RICE 14 | 21 | SORG 14 | 21 | CORN 14 | 21 | OAT 14 | 21 |
|---|---|---|---|---|---|---|---|---|---|---|---|---|---|---|---|
| Product of | 1 | 10 | 10 | 10 | 10 | 4 | 3 | 8 | 6 | NE | NE | 6 | 6 | 3 | 3 |
| Example 2 | .5 | 7 | 7 | 6 | 3 | 3 | 1 | 3 | 3 | 7 | 10 | 4 | 2 | 0 | 1 |
| | .25 | 8 | 10 | 0 | 0 | 0 | 1 | 0 | 2 | 7 | 8 | 3 | 2 | 0 | 0 |
| | .125 | | | | | | | | | | | | | | |

* = Average of two or more tests

TABLE II

Post-Emergence Screen

| Compound | #/Acre | WMSD | BDWD | MNGY | JMWD | PIGW | SOYB | WOAT | BNGS | CBGS | YLFX | JNGS | YNSG |
|---|---|---|---|---|---|---|---|---|---|---|---|---|---|
| Product of | 8 | 10 | 7 | 6 | 7 | — | 3 | 10 | 10 | 6 | 10 | 10 | 3 |
| Example 2 | 4 | 10 | 5 | 7 | 10 | 10 | 2 | 10 | 10 | 9 | 9 | — | 0 |
| | 2 | 10 | 3 | 2 | 10 | 10 | 2 | 5 | 10 | 10 | 9 | 10 | 0 |

TABLE II-continued

Post-Emergence Screen

| Compound | #/Acre | WMSD | BDWD | MNGY | JMWD | PIGW | SOYB | WOAT | BNGS | CBGS | YLFX | JNGS | YNSG |
|---|---|---|---|---|---|---|---|---|---|---|---|---|---|
| | 1 | 10 | 0 | 0 | 10 | 10 | 1 | 1 | 10 | 5 | 5 | 10 | 0 |

Abbreviations For Weeds
WMSD = Wild Mustard
BDWD = Bindweed
PIGW = Pigweed
JMWD = Jimsonweed
VTLF = Velvetleaf
MNGY = Morningglory
YLFX = Yellow Foxtail
BNGS = Barnyardgrass
JNGS = Johnsongrass
YNSG = Yellow Nutsedge
WOAT = Wild Oat
SPGT = Sprangletop
CTGS = Cheatgrass
SUBT = Sugar Beet
SOYB = Soybean
COTN = Cotton
PTBN = Pinto Bean
ALFA = Alfalfa
WHT = Wheat
SORG = Sorgum
QKGS = Quackgrass
CBGS = Crabgrass

We claim:

1. A compound of the formula

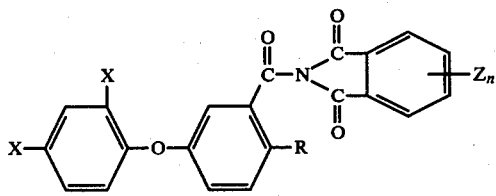

wherein X is chlorine, bromine or trifluoromethyl; Y is selected from the group consisting of hydrogen, chlorine, bromine, nitro and cyano; R is selected from the group consisting of nitro, alkylthio of up to six carbon atoms, chlorine, bromine and cyano; Z is selected from the group consisting of alkyl of up to six carbon atoms, chlorine, bromine and nitro; and n is an integer from 0 to 4.

2. The compound of claim 1, N-[2-nitro-5-(2-chloro-4-trifluoromethylphenoxy)benzoyl]phthalimide.

3. The compound of claim 1, N-[2-methylthio-5-(2-chloro-4-trifluoromethylphenoxy)benzoyl]phthalimide.

4. The compound of claim 1, N-[2-chloro-5-(4-trifluoromethylphenoxy)benzoyl]phthalimide.

5. The compound of claim 1, N-[2-cyano-5-(2,4-dichlorophenoxy)benzoyl]phthalimide.

6. The compound of claim 1, N-[2-nitro-5-(2-cyano-4-trifluoromethylphenoxy)benzoyl]phthalimide.

7. The compound of claim 1, N-[2-bromo-5-(2-nitro-4-bromophenoxy)benzoyl]phthalimide.

8. The compound of claim 1, N-[2-chloro-5-(2-chloro-4-trifluoromethylphenoxy)benzoyl]phthalimide.

9. A herbicidal composition comprising an inert carrier and in a quantity toxic to weeds a compound of claim 1.

10. A method of controlling weeds which comprises contacting said weeds or their locus with a herbicidal composition of claim 9.

* * * * *